United States Patent [19]

Ando et al.

[11] Patent Number: 5,030,009
[45] Date of Patent: Jul. 9, 1991

[54] OPTICAL GAS SENSOR

[75] Inventors: Itsuro Ando; Makoto Furuki; Lyong S. Pu, all of Kanagawa, Japan

[73] Assignee: Fuji Xerox Co., Ltd., Tokyo, Japan

[21] Appl. No.: 495,024

[22] Filed: Mar. 16, 1990

[30] Foreign Application Priority Data

Mar. 17, 1989 [JP] Japan .................................. 1-63494

[51] Int. Cl.$^5$ ............................................ G01N 21/25
[52] U.S. Cl. ....................................... 356/417; 422/55;
422/83; 250/361 C; 250/458.1
[58] Field of Search ........................ 356/417, 346, 432;
250/361 C, 461.2, 461.1, 458.1, 474.1, 459.1;
436/172; 422/55, 82.07, 83; 252/301.16;
204/153.1, 157.46, 418, 258, DIG. 11; 73/23.2,
23.37, 31.05; 430/58, 59; 558/427

[56] References Cited

U.S. PATENT DOCUMENTS

| | | | |
|---|---|---|---|
| Re. 31,879 | 5/1985 | Lubbers et al. | 422/82.07 |
| 4,857,472 | 8/1989 | Wolfbeis | 422/55 |
| 4,906,100 | 3/1990 | Rice et al. | 250/459.1 |

FOREIGN PATENT DOCUMENTS 62-35246  2/1987  Japan .

OTHER PUBLICATIONS

Patent Abstracts of Japan P-980, Dec. 21, 1989, vol. 13/No. 580, p. 70.

Primary Examiner—Vincent P. McGraw
Assistant Examiner—LaCharles P. Keesee
Attorney, Agent, or Firm—Finnegan, Henderson, Farabow, Garrett and Dunner

[57] ABSTRACT

An optical gas sensor comprises a light emitting element; a photo detecting element; a gas sensing element including a thin film containing an organic pigment, the gas sensing element responding to light emitted from the light emitting element to emit fluorescence or phosphorescence; and a filter for selectively picking up fluoroescence or phosphorescence, the gas sensing element and the filter being disposed in an optical path ranging from the light emitting element to the photo detecting element.

16 Claims, 1 Drawing Sheet

OPTICAL GAS SENSOR

BACKGROUND OF THE INVENTION

The present invention relates to an optical gas sensor using a thin film containing an organic pigment molecules as a gas sensing element.

Conventionally, gas sensors of the contact combustion type or the semiconductor type have been dominantly used. Recently, a gas sensor using light, such as an optode, has been proposed, and some applications thereof are realized (see Japanese Patent Application Unexamined Publication No. 62-35246). Further, it is known that some organic pigment molecules, when placed in an oxidizing gas or a reducing gas, interact with the gas with a certain selectivity, to change its electric or optical characteristic. There has been proposed a gas sensor of NOx or SOx which utilizes electric characteristic change of phthalocyanine, for example.

A gas sensor using light, such as an optode, has the following disadvantages. That is, a gas sensing portion is complicated in structure, a large laser device is required for a light source, and a photomultiplier tube is used for the photo detecting portion. Further, as far as we know, there is not yet developed the gas sensor using the organic pigment molecules which can stably sense gas many times by a simple means.

SUMMARY OF THE INVENTION

The present invention has been made to overcome the above disadvantages of a conventional sensor.

An object of the present invention is to provide an optical gas detector which is small in size, excellent in sensitivity, quick in response, and operable in a broad range of density.

Another object of the present invention is to provide an optical gas sensor which is easy and simple in manufacturing and measurement, and is stable and safe under different conditions.

Yet another object of the present invention is to provide an optical gas sensor in which unnecessary noise light is suppressed.

According to the present invention, there is provided an optical gas sensor comprising: a light emitting element; a photo detecting element; a gas sensing element including a thin film containing an organic pigment, the gas sensing element responding to light emitted from the light emitting element to emit fluorescence or phosphorescence; and a filter for selectively picking up fluorescence or phosphorescence, the gas sensing element and the filter being disposed in an optical path ranging from the light emitting element to the photo detecting element.

DETAILED DESCRIPTION OF THE INVENTION

Figure 1:
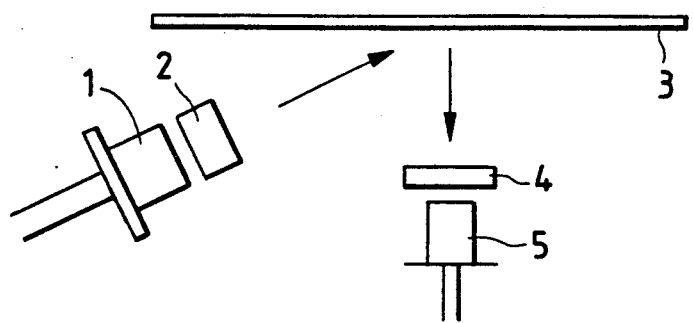
FIG. 1 is a view schematically showing an arrangement of an optical gas sensor according to the present invention.

The present invention will be described in detail.

A gas sensing element used in an optical gas sensor according to the present invention is formed of a thin film containing an organic pigment. In response to light from a light emitting element, the gas sensing element emits fluorescence or phosphorescence. The gas sensing element may be realized in a such a manner that a thin film containing organic pigment is placed on a support member. In accordance with the existence of a gas to be sensed, such as NOx, SOx, $Cl_2$, $O_3$ and $NH_3$, an intensity of fluorescence or phosphorescence emitted by the thin film reversely varies. Therefore, the gas can be sensed by measuring a color of the thin film or a variation of intensity of the emitted fluorescence or phosphorescence.

Particularly when the gas sensing element consisting of a thin film containing J association of squarylium is used, the gas sensor can sense NOx at a high sensitivity. The reason for this may be considered that an excited state in the J association resulted from light absorption can be quickly transferred in the J association, to increase a region covered as a trapping site of the excited state generated by the absorption of NOx. A pigment expressed by the general formula (I) is preferably used for the squarylium pigment.

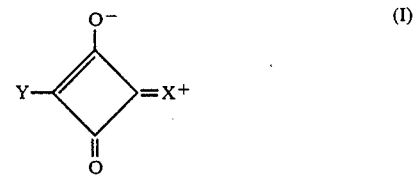

(where X and Y indicate chromophore).

In the general formula (I), the chromophore may be

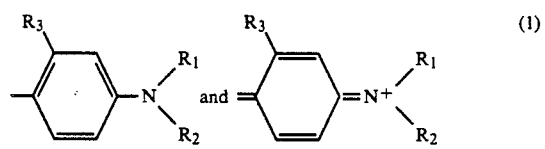

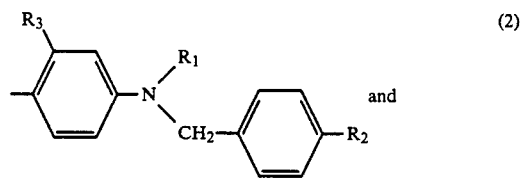

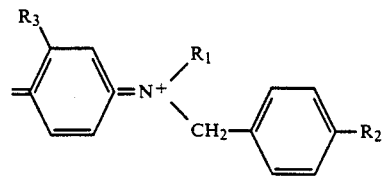

-continued (3) 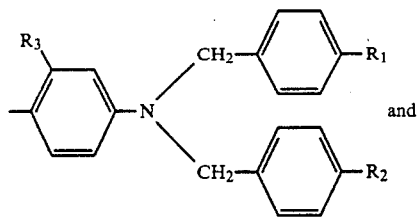 and (4) 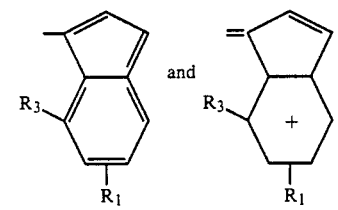

(5) 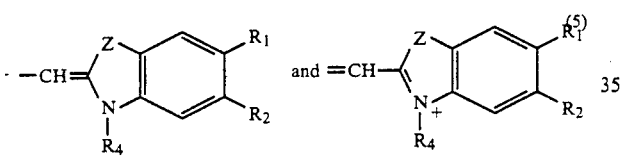

(6) 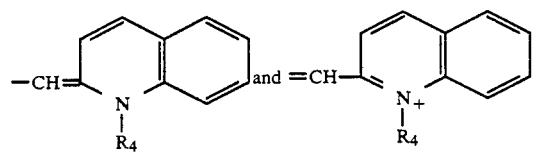

(7) 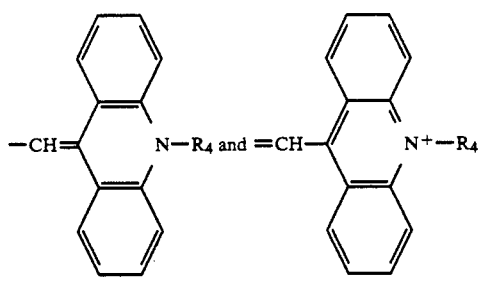

(8) 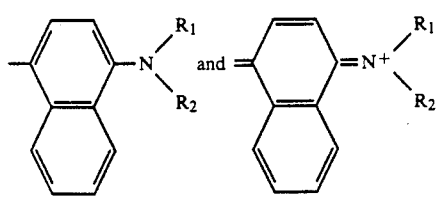

-continued (9) 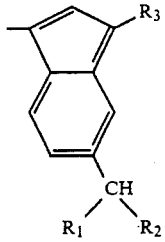 and 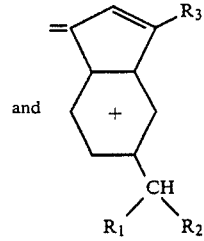

(10) 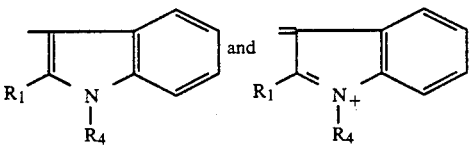

(11) 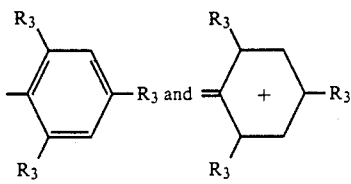

(12) 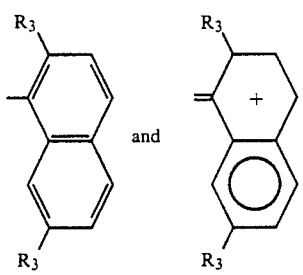

(In the formula, $R_1$ and $R_2$ are equal to or different from each other. $R_1$ and $R_2$ represent hydrogen atom, $C_nH_{2n+1}$, $C_nH_{2n}OH$, $C_nH_{2n-1}$, $C_nH_{2n-2}$ (n=1 to 20), chlorine atom, fluorine atom or bromine atom; $R_3$, hydrogen atom, hydroxyl group, $C_nH_{2n+1}$ (n=1 to 20), methoxy group, flourine atom, chlorine atom or bromine atom; $R_4$, hydrogen atom, hydroxyl group, $C_nH_{2n+1}$ (n=1 to 20), or methoxy group; Z, $C(CH_3)_2$, O, S or Se.)

Specific examples of the squarylium are referred to in Japanese Patent Application No. 63-69666.

In the optical gas sensor according to the present invention, the light emitting element, which is used as an exciting light source to cause the thin film to emit fluorescence or phosphorescence, may be a semiconductor laser element or a LED (light emitting diode).

The filter for separating fluorescence or phosphorescence from an exciting light is disposed in the optical path between the gas sensing element and the light emitting element. This filter is a filter of such a characteristic as to attenuate the light emitted from the light emitting element, but to transmit mainly fluorescence or phosphorescence emitted from the gas sensing element. The filter is preferably a filter of such a characteristic as to attenuate a light whose wave length is longer than that of the fluorescence or phosphorescence emitted from the gas sensing element.

When the light emitted by the light emitting element contains other components than the light of a wave length necessary for the excitation, a filter to suppress such components of light may be further provided. A filter having such a characteristic as to transmit lights whose wave lengths close to those of major lights emitted from the light emitting element, and to attenuate other lights than the lights, may be disposed in the optical path between the light emitting element and the gas sensor. In this case, the filter is preferably disposed in such a way that light is incident on the filter at an incident angle with respect to the direction orthogonal to the surface of the filter.

The optical gas sensor according to the present invention can sense a gas to be sensed by measuring a reversible change of color or a reversible change of intensity of fluorescence or phosphorescence of the thin film containing an organic pigment, which results from the contact of the thin film with the gas. To be more specific, an exciting light emitted from the light emitting element reaches the organic pigment contained in the thin film of the gas sensing element. The exciting light excites the organic pigment to cause it to emit fluorescence or phosphorescence. In this case, when the thin film contacts the gas, such as $NO_x$, $SO_x$, $Cl_2$, $O_3$, and $NH_3$, the wave lengths of the absorption spectrum of lights emitted from the gas sensing element reversely vary or the intensity of the fluorescence or phosphorescence reversely varies. The light from the gas sensing element is applied to the photo detecting element, through the filter for separating the fluorescence or phosphorescence from the exciting light. The reversible color variation of the exciting light from the thin film or the intensity variation of the fluorescence or phosphorescence emitted from the thin film are measured by the photo detecting element. In this way, the gas is sensed.

FIG. 1 schematically shows an arrangement of an optical gas sensor according to the present invention. In the figure, reference numeral 1 designates a light emitting element; 2, a lens; 3, a gas sensing element consisting of a thin film containing an organic pigment; 4, a filter for filtering out an exciting light; 5, a photo detecting element.

An exciting light emitted from the light emitting element 1 is concentrated on the gas sensing element 3 by the lens 2. In response to the light, a thin film on the gas sensing element 3 emits fluorescence or phosphorescence. The emitted fluorescence or phosphorescence passes through the filter 4 and reaches the photo detecting element 5. In turn, it is converted into an electrical signal by an electric circuit (not shown). In this case, when the gas sensing element 3 contacts a specific gas (e.g., $NO_2$), the intensity of the fluorescence or phosphorescence emitted from the gas sensing element 3 varies. Thus, a gas concentration can be detected in the form of an electric signal.

In the present invention, the gas sensing element 3 is constructed such that a thin film containing an organic pigment is formed on a substrate made of glass, for example. Such an organic pigment is preferable that when receiving a light of a wave length between 600 nm and 760 nm, it emits fluorescence or phosphorescence whose intensity peak is at 770 nm or so.

In connection with this, the light emitting element 1 is preferably an LED or semiconductor laser element which emits mainly lights of wave lengths ranging from 600 nm to 760 nm. The LED or the laser element may be used as a small exciting light source.

As a matter of course, the photo detecting element 5 must be sensitive to the fluorescence or phosphorescence whose intensity peak is at 770 nm or so.

The lens 2 must be capable of effectively concentrating the light from the light emitting element 1 on the gas sensing element 3 while preventing it from diverging. The lens 2 also intensifies the fluorescence or phosphorescence. The lens 2 may be formed integral with the light emitting element 1.

There is the possibility that the exciting light from the light emitting element 1 reflects or diverges on the gas sensing element 3, and enters the photo detecting element 5. To prevent such light from entering the photo detecting element 5, the filter 4 is used. With use of the filter 4 filtering out the exciting light and the diverging light, if the photo detecting element is sensitive to the exciting light, a proportion of the fluorescence or phosphorescence becomes large in the light entering the photo detecting element 5, and accordingly the resultant electric signal contains a less amount of noise.

To more effectively concentrate the flourescence or phosphorescence, a lens may be placed in front of the photo detecting element 5 or the filter 4. In this case, the lens and the photo detecting element may be integral with each other.

In the optical gas sensor of the present invention, in order that the photo detecting element 5 can effectively receive the fluorescence or phosphorescence emitted from the gas sensing element 3, the light emitting element 1, lens 2, gas sensing element 3, filter 4 and the photo detecting element 5 must be disposed in this order. Further, to reduce the size of the sensor as small as possible and to obtain a large electric signal, those components must be disposed as closely as possible. In this case, to prevent the exciting light from entering the photo detecting element, it is preferable to dispose the photo detecting element 5 out of an optical path of the exciting light reflected at the gas sensing element 3. More specifically, such an arrangement of those components is preferable that the filter 4 and the photo detecting element 5 are formed integral with each other and disposed in the direction orthogonal to the gas sensing element 3, and the light emitting element 1 and the lens 2 are also monolithically formed and disposed at an appropriate angle (several degrees to several tens degrees) with respect to that orthogonal direction.

Figure 2:
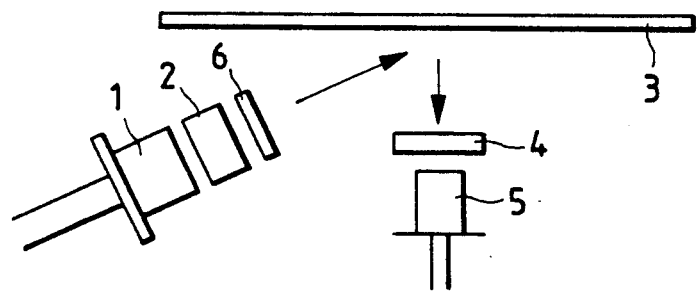
FIG. 2 is a view schematically showing an arrangement of another optical gas sensor according to the present invention.

The light derived from the light emitting element 1 containing the components of light whose wave lenghts are within 600 to 760 nm, often contains the light components whose wave lengths are longer than the above ones. In the case of the light emitting element 1 using a material in the family of GaAs, the light emitted by the element consists of major components of light whose peaks are between 600 nm and 760 nm, and a slight photo luminescence having small peaks at about 890 nm. The intensity of the peak of the photo luminescence is small, e.g., 1/100 that of the major components of the light, but it serves as a noise when the fluorescence or phosphorescence is measured. To remove the noise light, a band-pass filter having such a characteristic as to transmit only the fluorescence or phosphorescence of 780 nm or so, but also to attenuate the light whose wave length is shorter and longer than the above wavelength, is used for the filter 4. Alternatively, a filter to attenuate the light whose wave length is longer than about 780 nm is additionally used. In the latter case, the filter to remove the light of the long wave length may be located at any place in the optical path between the light emitting element 1 and the photo detecting element 5. In the light of space saving, however, it is preferable to place it as shown in FIG. 2. That is, a filter 6 to cut off the light of the long wave length is placed between the lens 2 and the gas sensing element 3. Particularly when a semiconductor laser element is used for the light emitting element, it is preferable that the filter 6 is slightly slanted with respect to the path of the exciting light, not orthogonal to the path, as shown in FIG. 2. The filter 6 so slanted can prevent the light reflected on the surface of the filter 6 from returning to a light emitting part of the semiconductor laser element. In FIG. 2, other symbols than the symbol 6 designate like portions in FIG. 1.

In FIGS. 1 and 2 showing the arrangements of the optical gas sensors according to the present invention, those components thus arranged in each sensor are packed into a small box (not shown).

In the case of each gas sensor as mentioned above, the box per se is placed in a gas to be sensed. Some time is taken until the box is completely filled with the gas. In other words, a gas sensing response of the gas sensor is slow. To solve this problem, a gas guide member is preferably provided around the gas sensing element so as to allow the gas to flow only around the gas sensing element.

Figure 3:
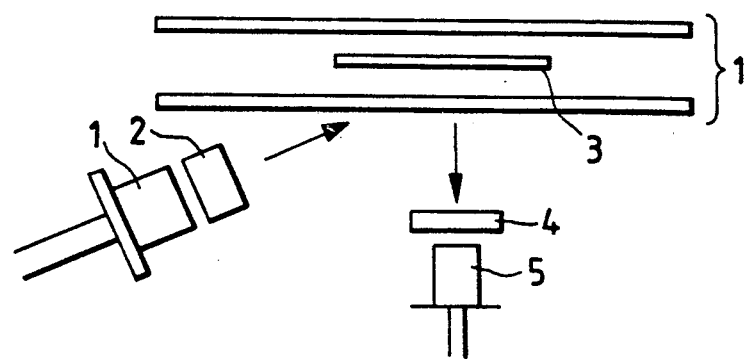
FIG. 3 is a view showing an optical gas sensor according to an embodiment of the present invention.

A specific example of the gas sensor using such a gas guide member is shown in FIG. 3. As shown, a gas guide member 7 is provided around the gas sensing element 3, with a minimum dead space, thus improving the response. Further, the light emitting element 1, lens 2, filter 4, photo detecting element 5, and the like are separated from the sensed gas. Because of this feature, the resultant gas sensor is more reliable.

More specific examples of the present invention will be described.

EXAMPLE 1

Squarylium pigment as expressed below

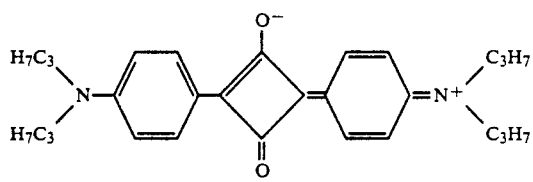

and arachic acid ($C_{19}H_{39}COOH$) were put into a chloroform solution at the mol ratio of 1:1. A solution whose concentration is about $8\times10^{-4}M$ was prepared. By using this solution, a film was formed by an LB film forming method. In this way, a gas sensing element made of a J association of the squarylium pigment was formed. More specifically, the solution of about 200 ul is spread on a water surface, and a glass substrate is moved up and down through the interface of the air and the solution, thereby to form a gas sensing film on the glass substrate.

The light emitting element as an exciting light source was a semiconductor laser element (commercially available) emitting a light whose peak intensity is at 670 nm or so. A plastic lens for collecting the light emitted from the semiconductor laser element is placed in front of the laser element. The photo detecting element was a silicon photo diode commercially available. An exciting light cutting filter was mounted to the front of the silicon photo diode. The filter was a filter with such a structure that an interference film is vapor deposited over a color glass filter. The filter attenuates or cuts off the lights whose wave lengths are shorter than 720 nm or so. Those components were arrayed as shown in FIG. 1. Specifically, a combination of the exciting light cut filter and the silicon photo diode was located 5 to 10 mm apart from the gas sensing element, while being oriented in the direction substantially orthogonal to the gas sensing element.

A combination of the semiconductor laser element and the lens was arranged so that the exciting light enters the gas sensing element at an incident angle of about 60° with respect to the direction orthogonal to the gas sensing element. The components, together with a semiconductor drive circuit and a photo diode drive circuit, were assembled into a box with a gas inlet and blackened inner surface so that the optical gas sensor was formed.

The optical gas sensor thus assembled was operated. The semiconductor laser element was driven to emit an exciting light. The exciting light hit the gas sensing element, and caused it to emit fluorescence or phosphorescence. The fluorescence or phosphorescence was applied to the photo diode. In turn, a current in the order of $10^{-9}$ A flowed in the photo diode, and was amplified by an electric circuit and outputted as a voltage signal of about 1 V.

Under this condition, NOx gas of 0.1 to 100 ppm was introduced into the box through its gas inlet. The signal voltage was varied in accordance with a concentration of the introduced gas. Thus, a concentration of the NOx gas could be qualitatively measured.

EXAMPLE 2

Another optical gas sensor was manufactured by the components similar to those of the first example, except for the exciting light cut filter. The filter was a bandpass filter to transmit the lights whose wave lengths are substantially within a range from 720 nm to 850 nm. Those components were arranged and assembled into a box, as in the first example. A voltage signal outputted when NOx gas is not present was set at a level substantially equal to that of the first example. Under this condition, NOx gas was introduced into the box. The signal voltage was varied in accordance with a concentration of the gas. Thus, the qualitative measurement of a concentration of gas could be done. The variation of the signal voltage was greater than that in the first example. Additionally, it was confirmed that the lights whose amplitude peaks are at 890 nm or so were cut off to result in improvement of an S/N ratio.

EXAMPLE 3

The light emitting element, lens, gas sensing element, exciting light cut filter, and the photo detecting element were similar to those in the first example, and arranged also as in the first example. An infrared rays cut filter for cutting off the lights of wave lenghts longer than 800 nm, was placed in front of the lens. The infrared rays cut filter was slanted so that the exciting light enters the infrared rays cut filter at an incident angle of about 20°. A voltage signal outputted when NOx gas is not present was set at a level substantially equal to that of the first example. Under this condition, NOx gas was introduced into the box. The signal voltage was varied in accordance with a concentration of the gas. Thus, the qualitative measurement of a concentration of gas could be done. The variation of the signal voltage was greater than that in the first example. That is, it was confirmed that the lights whose amplitude peaks are at 890 nm or so were cut off to result in improvement of an S/N ratio.

EXAMPLE 4

In a gas sensor of this example, the gas sensing element was confined in a gas guide member of transparent glass. Except this, the components and the arrangement of them were similar to those of the first example. NOx gas was introduced into the box. The signal voltage was varied in accordance with a concentration of the gas. Thus, the qualitative measurement of a concentration of gas could be done. The response of this example was less than 1/10 of that of the first example.

EXAMPLE 5

In this example, an LED whose front end is shaped like a lens and peak wave length is 660 nm or so was used in place of the semiconductor laser element. A photo diode with a lens was used for the photo detecting element. Other components, such as the gas sensing element and the exciting light cur filter, and the arrangement of them were similar to those in the first example.

The components, together with a semiconductor drive circuit and a photo diode drive circuit, were assembled into a box with a gas inlet and a blackened inner surface.

The optical gas sensor thus assembled was operated. The LED was lit on to emit an exciting light. The exciting light hit the gas sensing element, and caused it to emit fluorescence or phosphorescence. The fluorescence or phosphorescence was applied to the photo diode, and outputted in the form of a voltage signal. Under this condition, NOx gas of 0.1 to 100 ppm was introduced into the box through its gas inlet. The signal voltage was varied in accordance with a concentration of the introduced gas. Thus, the concentration of the NOx gas could be qualitatively measured.

As seen from the foregoing description, in the optical gas sensor according to the present invention, the gas sensing element including a thin film containing an organic pigment, the gas sensing element responding to light emitted from the light emitting element to emit fluorescence or phosphorescence, and the filter are disposed in the optical path ranging from the light emitting element to the photo detecting element. The gas sensor thus arranged may easily sense a gas by utilizing a reversible physical and chemical variation due to the interaction of the gas sensing element with the gas. Further, it may qualitatively measure the gas by using the same variation.

The optical gas sensor according to the present invention is excellent in optical sensitivity, stability, and response, and is operable in a broad range of gas concentrations. Further, the gas sensor is easy to manufacture, low in cost, and advantageous in connection with environmental matter. Accordingly, the gas sensor may find a variety of applications. Further, since the gas sensor utilizes light, it is stable against electric, magnetic and chemical interference.

It is evident that the optical gas sensor according to the present invention is applicable for sensing not only NOx gas, but also an oxidizing gas, such as SOx, $Cl_2$, and $O_3$, and a reducing gas, such as $NH_3$. The thin film of the gas sensor changes also its electric characteristic, etc. in accordance with the change of color. Therefore, the gas sensor may be used as a gas sensing element, which is used in a conventional electric gas sensor.

Further, a semiconductor laser element or an LED may be used for the light emitting element, and a photo diode may be used for the photo detecting element. Use of those small components leads to the reduction in size and cost of the gas sensor, and improvement of reliability.

What is claimed is:

1. An optical gas sensor comprising:
    a light emitting element;
    a photo-detecting element;
    a gas sensing element including a thin film formed by an LB film forming method containing an organic pigment, said gas sensing element responding to light emitted from said light emitting element to emit fluorescence or phosphorescence; and
    a first filter for selectively picking up the fluorescence or phosphorescence, said gas sensing element and said filter being disposed in an optical path ranging from said light emitting element to said photo detecting element.

2. An optical gas sensor according to claim 1, further comprising a gas guide means being disposed around said gas sensing element so as to guide gas only around said gas sensing element.

3. An optical gas sensor according to claim 1, in which said organic pigment contained in said thin film of said gas sensing element has a structure of J association.

4. An optical gas sensor according to claim 1, in which said organic pigment contained in said thin film of said gas sensing element is squarylium pigment.

5. An optical gas sensor according to claim 1, in which said light emitting element is a semiconductor laser element of a light emitting diode.

6. An optical gas sensor according to claim 1, in which said first filter has such a characteristic as to attenuate the light emitted from said light emitting element, but to transmit fluorescence or phosphorescence emitted from said gas sensing element.

7. An optical gas sensor according to claim 1 or 6, in which said first filter has such a characteristic as to attenuate a light whose wave length is longer than that of the fluorescence or phosphorescence emitted from said gas sensing element.

8. An optical gas sensor according to claim 1 or 2, further comprising a second filter for transmitting a spectrum of light having a wavelength close to a wavelength of a light emitted from said light emitting element, and attenuating lights other than the spectrum of light, said second filter being disposed in the optical path between said light emitting element and said gas sensor.

9. An optical gas sensor according to claim 8, in which said second filter is disposed in such a way that light is incident on said second filter at an incident angle with respect to the direction orthogonal to the surface of said second filter.

10. An optical gas sensor according to claim 1, wherein said light emitting element emits light having a wavelength between 600 nm and 760 nm.

11. An optical gas sensor according to claim 1, wherein said organic pigment in said thin film on said gas sensing element receives light having a wavelength between 600 nm and 760 nm, and emits fluorescence or phosphorescence having an intensity peak of 770 nm.

12. An optical gas sensor according to claim 1, wherein said photo detecting element is sensitive to fluorescence or phosphorescence having an intensity peak of 770 nm.

13. An optical gas sensor according to claim 1, wherein said thin film formed by an LB film forming method includes a film of squarylium, formed by spreading a solution of squarylium on a water surface and moving a substrate of said gas sensing element through said solution.

14. An optical gas sensor comprising:

light emitting means for emitting light;

gas sensing means disposed in a gas atmosphere having a thin film containing a J-association of squarylium, for receiving the emitted light and emitting fluorescence or phosphorescence, said light emitting means and gas sensing means defining a first optical path;

photo detecting means for detecting the emitted fluorescence or phosphorescence, said photo detecting means and gas sensing means defining a second optical path; and a filter element disposed in one of said first and second optical paths.

15. An optical gas sensor comprising:

light emitting means for emitting light;

gas sensing means disposed in a gas atmosphere having a thin film containing an organic pigment for receiving the emitted light and emitting fluorescence or phosphorescence, said thin film defining a plane, said light emitting means emitting said light in a first optical path forming an angle relative to the plane defined by said thin film;

photo detecting means for detecting the emitted fluorescence or phosphorescence, said photo detecting means disposed in a second optical path of said fluorescence or phosphorescence generally orthogonal to the plane defined by said thin film; and a filter element disposed in one of said first and second optical paths.

16. An optical gas sensor comprising:

a light emitting element;

a photo-detecting element;

a gas sensing element including a thin film containing an organic pigment including a J-association of squarylium, said gas sensing element responding to light emitted from said light emitting element to emit fluorescence or phosphorescence; and a first filter for selectively picking up the fluorescence or phosphorescence, said gas sensing element and said filter being disposed in an optical path ranging from said light emitting element to said photo-detecting element.

* * * * *